United States Patent
Zhang et al.

(10) Patent No.: US 7,998,197 B2
(45) Date of Patent: Aug. 16, 2011

(54) OFF-AXIS ANTI-REFLECTIVE INTRAOCULAR LENSES

(75) Inventors: Xiaoxiao Zhang, Fort Worth, TX (US); Kamal K. Das, Arlington, TX (US)

(73) Assignee: Novartis AG, Basel (CH)

( * ) Notice: Subject to any disclaimer, the term of this patent is extended or adjusted under 35 U.S.C. 154(b) by 81 days.

(21) Appl. No.: 12/171,760

(22) Filed: Jul. 11, 2008

(65) Prior Publication Data

US 2009/0018651 A1    Jan. 15, 2009

Related U.S. Application Data

(60) Provisional application No. 60/949,741, filed on Jul. 13, 2007.

(51) Int. Cl.
*A61F 2/16* (2006.01)
(52) U.S. Cl. .................. 623/6.17; 623/6.62; 623/6.11
(58) Field of Classification Search .................. 623/6.17, 623/6.26, 6.62; 359/581, 586, 588–590; 351/160 R, 161–165, 168–169, 171
See application file for complete search history.

(56) References Cited

U.S. PATENT DOCUMENTS

| | | | | |
|---|---|---|---|---|
| 4,609,267 A * | 9/1986 | Deguchi et al. | ............... | 351/163 |
| 4,940,602 A * | 7/1990 | Taniguchi et al. | ............ | 427/489 |
| 6,406,739 B1 | 6/2002 | LeBoeuf et al. | ............. | 427/2.24 |
| 6,632,887 B2 | 10/2003 | LeBoeuf et al. | ............... | 525/203 |
| 6,835,204 B1 * | 12/2004 | Stork et al. | ..................... | 623/6.25 |
| 6,851,803 B2 * | 2/2005 | Wooley et al. | ................ | 351/159 |
| 7,217,289 B2 | 5/2007 | Coronco | ...................... | 623/6.17 |
| 2001/0018612 A1 * | 8/2001 | Carson et al. | ................. | 623/5.11 |
| 2007/0268450 A1 * | 11/2007 | Futamura et al. | ......... | 351/160 R |

FOREIGN PATENT DOCUMENTS

| | | |
|---|---|---|
| CN | 1799522 A | 11/2005 |
| DE | 34 28 895 | 2/1986 |
| EP | 0 193 269 | 9/1986 |
| EP | 0 278 060 | 8/1988 |
| WO | 96/04216 | 2/1996 |

OTHER PUBLICATIONS

PCT/US2008/069768 International Search Report with mailing date Apr. 21, 2009.
PCT/US2008/069768 Written Opinion with mailing date Apr. 21, 2009.

* cited by examiner

*Primary Examiner* — David H Willse
*Assistant Examiner* — Tiffany Shipmon
(74) *Attorney, Agent, or Firm* — Scott A. Chapple

(57) ABSTRACT

Exemplary embodiments provide a coated intraocular lens that has a lens body with a first refractive index and an anti-reflective coating. The coating covers at least a portion of the lens body and has a second index of refraction that is less than the first index of refraction of the lens body. The anti-reflective coating reduces the intensity of reflections produced from off axis light incident on the lens body by at least a factor of 2.5 times and enhancing light transmission.

16 Claims, 3 Drawing Sheets

OFF-AXIS ANTI-REFLECTIVE INTRAOCULAR LENSES

This application claims priority to U.S. Provisional Application, U.S. Ser. No. 60/949,741 filed Jul. 13, 2007.

TECHNICAL FIELD

The embodiments described herein generally relate to intraocular lenses and more particularly relate to intraocular lenses that are anti-reflective to off-axis light.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

Several eye conditions may require vision correction by insertion of an intraocular lens ("IOL"). For example, when trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an IOL. In general, the procedures for cataract lens removal and IOL implantation have become common place and virtually routine. Other conditions may not require removal of the natural lens from the eye but insertion of a phakic intraocular lens in either the anterior chamber (i.e., in front of the natural lens and the iris) or the posterior chamber (i.e., in front of the natural lens, but behind the iris).

IOLs may also be "bifocal" to assist those persons who have developed age-related presbyopia. These IOLs have a more complex optic design than standard IOLs that lack bifocal capability. Some of the bifocal IOLs have a central optic region that is smooth and curved, like other standard IOLs, with a surrounding light-diffracting area. For example, the ReSTOR® IOL (ReSTOR is a registered trademark of Alcon Labs, Fort Worth, Tex.) uses apodized diffractive optics to provide improved image quality at both distance and near. The apodized diffractive optics technology is applied to an acrylic IOL, long in service as a standard IOL, and has been implanted in over 21 million cases since 1994. An apodized diffractive IOL has a series of minute, sawtooth shaped projections 16 arrayed in a peripheral region 14 around a central optic region 12 of an IOL 10, as shown in FIG. 1. These projections 16 produce walls 18 that extend upward from the lens surface and that diffract light to facilitate the bifocal effect.

Some IOL-wearers have noted reflectance of light that are cosmetically undesirable for persons who are on camera or photographed. Some other IOL-wearers have noted unwanted visual images that appear to originate from IOL-related reflective phenomena. These phenomena may include glare, halos, dysphotopsia, and reflection, among others. While the unwanted images and cosmetically inappropriate reflectance do not pose vision handicaps, they each nonetheless present an issue that remains unresolved in the market place.

Accordingly, it is desirable to develop IOLs that have an anti-reflective property to minimize unwanted IOL-related reflective phenomena such as unwanted visual images. In addition, it is desirable that the anti-reflective property be readily integrated into existing IOLs. Furthermore, other desirable features and characteristics of the off-axis anti-reflective IOLs will become apparent from the subsequent detailed description and the appended claims, taken in conjunction with the accompanying drawings and the foregoing technical field and background.

BRIEF SUMMARY

Exemplary embodiments provide a coated intraocular lens that has a lens body with a first refractive index and an anti-reflective coating. The coating covers at least a portion of the lens body and has a second index of refraction that is less than the first index of refraction of the lens body. The anti-reflective coating reduces the intensity of reflections produced from off axis light incident on the lens body by at least a factor of 2.5 times and increases light transmission to enhance desired retinal images.

Another example of an embodiment provides a coated intraocular lens that has a diffractive lens body with a first refractive index, and an anti-reflective coating over at least a diffractive portion of the diffractive lens body. The anti-reflective coating has a lower index of refraction than the first refractive index of the diffractive lens body. In addition, the anti-reflective coating reduces an intensity of reflections produced from incident off axis light on the lens body by at least a factor of 2.5 times.

Another exemplary embodiment provides a coated intraocular lens that has a lens body having a refractive index in the range from about 1.52 to about 1.60; and an anti-reflective coating over at least a portion of the lens body. The anti-reflective coating has a first coating layer adhering to the lens body and a second coating layer adhering to the first coating layer. The first coating layer has a lower index of refraction than the lens body and the second coating layer has a lower refractive index than the first coating layer.

BRIEF DESCRIPTION OF THE DRAWINGS

Various embodiments will hereinafter be described in conjunction with the following schematic, not-to-scale drawing figures, wherein like numerals denote like elements.

DETAILED DESCRIPTION

The following detailed description is merely exemplary in nature and is not intended to limit the described embodiments or the application and uses of the described embodiments. Furthermore, there is no intention to be bound by any expressed or implied theory presented in the preceding technical field, background, brief summary or the following detailed description.

In the specification and claims, the term "IOL" or "intraocular lens" should be read broadly to include all IOLs, for example phakic IOLs, bifocal IOLs, multifocal IOLs, and standard IOLs.

As indicated above, there are at least two types of undesirable optic phenomena caused by lens surface properties. In one type, surface reflection from the lens may allow others to see a bright reflection in the wearer's pupil, and this reflection might also be visible in photographs or on video displays. Accordingly, it may be of cosmetic concern for some wearers. The second type of undesirable optic phenomena has visual performance implications for some wearers and is manifested, for example as flares and halos. The surface reflections may cause a reduction in retinal contrast and/or other visual disturbance. In the case of a diffractive IOL or others that have modulated surfaces, the IOL structural features, such as walls in a bifocal IOL, can reflect light into the posterior portion of the eye and create the visual disturbance when the light impinges the retina.

Figure 1:
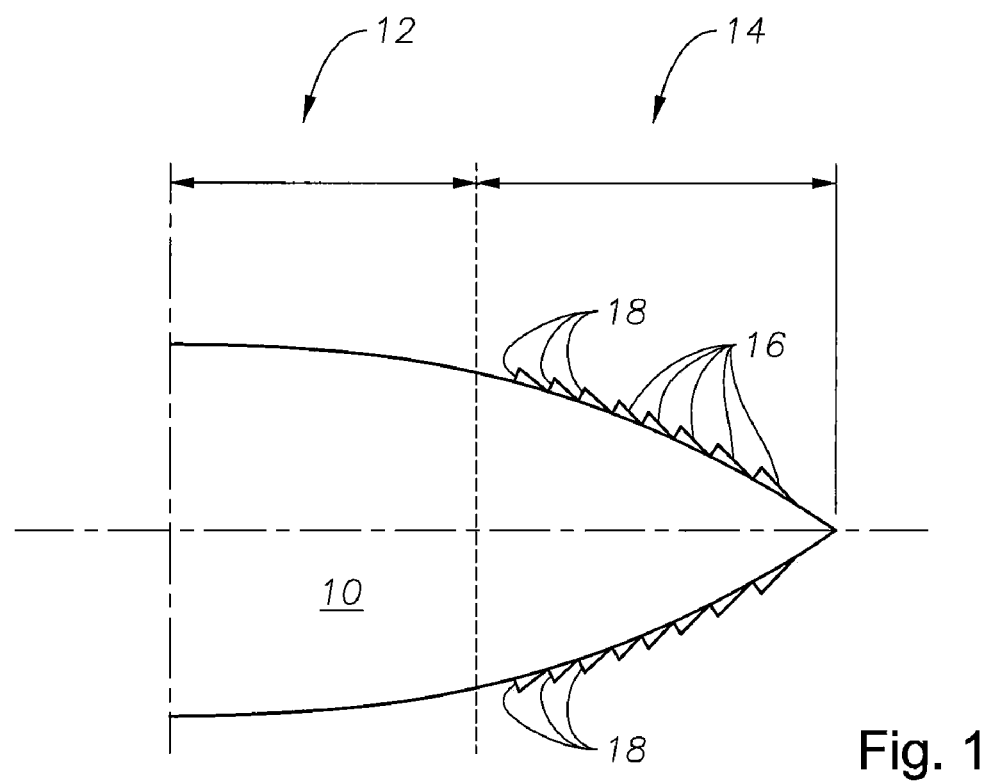
FIG. 1 is an enlarged view of a portion of a prior art bifocal intraocular lens.
Figure 2:
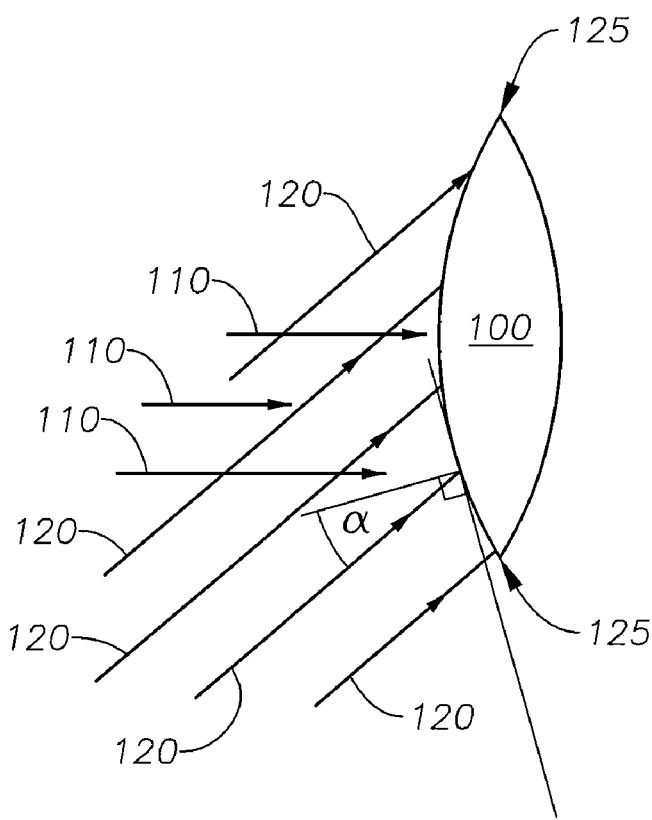
FIG. 2 is a side view of a lens body depicting areas of the lens body and incident light angles.

It is further important to distinguish between reflective phenomena that may arise from direct light (i.e., incident at an angle of near 90° to the lens surface), also referred to herein as "axial light," and reflective phenomena that may arise from "off axis" incident light that strikes the lens surface and the lens edge from an angle less than 90°. FIG. 2 illustrates light incident on an intraocular lens body 100. The light rays 110 may be regarded as axial while the light rays 120 are at an angle α° to (a tangent to) the lens surface and are regarded as off axis light rays. The angle α° may vary typically in the range from about 15° to about 50°, but may range more widely, depending upon lens material, to the range from about 10° to about 70°. As also shown in FIG. 2, the axial light rays 110 and the off axis light rays 120 may be incident anywhere on the lens body 100. However the incidence of off axis light rays presents visual disturbances, with respect to reflections, especially if the light rays 120 are incident at the edges of the lens 125. These disturbances may present "ghost images" and may have motion opposite to the real images. These disturbances are often associated with wearers that have larger pupils.

Figure 3:
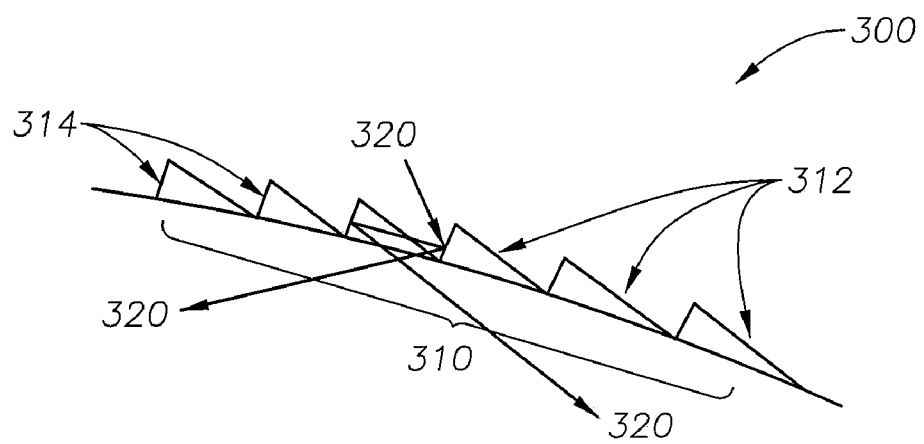
FIG. 3 is an enlarged portion of a diffractive lens body depicting light scatter from surface walls.

As shown in FIG. 3, an enlarged portion of a diffractive surface 310 of diffractive IOL 300, that includes a series of saw-tooth shaped projections 312 with walls 314. Light ray 320 incident upon a wall 314 may be at least partially reflected forward to impinge upon an adjacent wall 314 and be reflected thereafter, as shown, or may be reflected directly from wall 314 that it initially impinges, as shown. This light scattering may cause unwanted flares, halos and other phenomena generally referred to herein as "reflections." Elimination of reflections may improve wearer acceptance and satisfaction.

Figure 4:
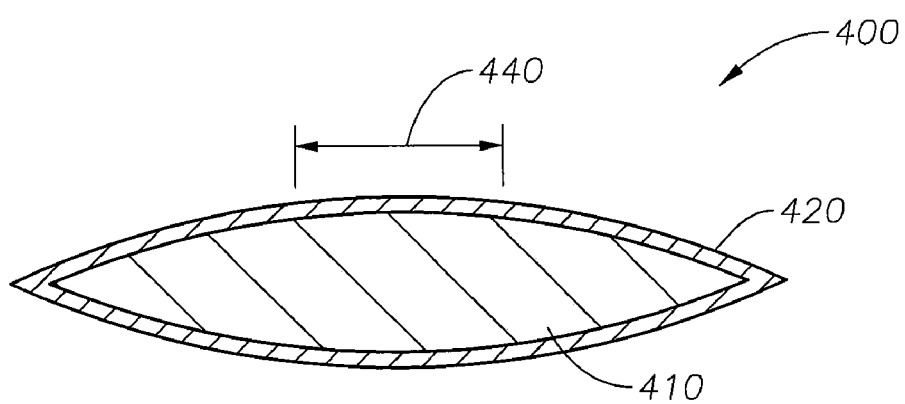
FIG. 4 is a cross section of an exemplary embodiment of an IOL lens body with a single coating.

According to exemplary embodiments, an anti-reflective coating effective for selective light incident angle ranges may be applied to IOLs. Accordingly, the anti-reflective coating may be functional only for off-axis light, for example. These embodiments are especially useful in younger patients and other patients that have larger pupils. These patients with larger pupils expose a larger visual field angle and are accordingly more likely to experience off-axis light sources. According to an example of an embodiment, a ReSTOR® IOL is coated with an anti-reflective coating to reduce or eliminate off-axis light reflectance phenomena. FIG. 4 illustrates an exemplary embodiment of an anti-reflective coated IOL lens 400 with the lens body 410 coated with a single layer anti-reflective coating 420. While the illustrated coating 420 covers the entire lens body 410, the coating may only cover peripheral regions of the lens body 410. For example, the central region 440 of the lens body may be masked off during the process of coating the lens, or some other appropriate technique may be applied.

With regard to off axis reflections of light, in general, the reflectance from a surface or interface of two media may be described by two equations:

$$R = \frac{r_1^2 + r_2^2 + 2r_1 r_2 \cos(X)}{1 + r_1^2 + r_2^2 + 2r_1 r_2 \cos(X)} \quad (A1)$$

where, $r_1$, $r_2$ are amplitude reflection coefficients and X is the phase.
The quantity X is defined as $$X = \frac{4\pi n t}{\lambda} \cos(\alpha) \quad (A2)$$

where, n is the refractive index of the coating, t is the coating thickness, λ is the wavelength and α is the incidence angle of light. The objective is to minimize the reflectance, such that the transmittance will increase. Use of these two equations allows the selection of appropriate anti-reflective coatings effective for minimizing or eliminating reflections from incident off axis light on a lens surface.

Exemplary embodiments provide anti-reflective coated high-refractive index IOLs that reduce off axis reflectance. These high-refractive index IOLs have a refractive index in the range from about 1.46 to about 1.60. The refractive index of a coating applied to an IOL is less than that of the IOL to achieve anti-reflection properties. For example, a lens refractive index of 1.52, the coatings may be about 85 nm thick, based on the above equations (A1), (A2). Coating thickness is directly related to the off axis angle of interest for reflection reduction. As an example, an anti-reflective coating of with a thickness of about 100 nm could reduce reflections of axial or axial light. For the same refractive indexes of lens and coating, a coating thickness of only 70 nm would suffice to similarly reduce reflections of 40 degree off axis light to the same extent as the 100 nm coating.

Figure 6:
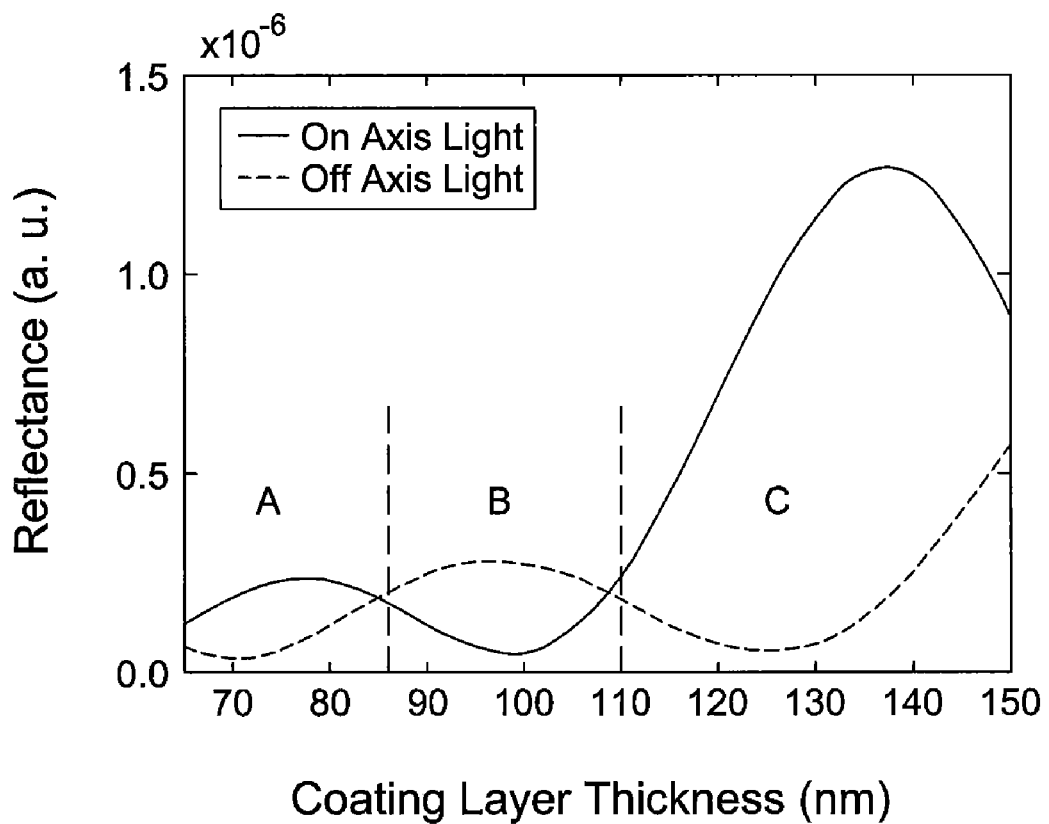
FIG. 6 is a graphical illustration of equations (A1) and (A2) that indicate the selected zones of acceptable coating thickness for minimizing off axis light reflections.

In general, for purposes of light reflection, coating thickness and refractive index are related, as seen from the above equations. A primary purpose of the coatings of the present technology is to reduce reflections from off axis light while minimizing any adverse effects on the transmission of off axis light and on the transmission of axial light. Accordingly, for a range of refractive indices, a range of coating thicknesses may be established that achieve this purpose using equations (A1) and (A2). Referring to the graph of FIG. 6, the curves represent the variation of reflectance of axial (on axis) light and off axis light with coating thickness for an exemplary embodiment of a coating that includes two coating layers of equal thickness. The x-axis of the graph represents the thickness of the coating layers, which are identical, not the total coating thickness. (The total coating thickness would be twice the coating layer thickness, in this case.) In the zone marked "A," the reflectance of off axis light is low, and the reflectance of axial light is tolerable but greater than in zone B. In zone B the reflectance of off axis light is higher than in Zone A and is therefore less desirable if the objective is to reduce such reflectance. However, the reflectance of axial light is lower than in Zone A. Thus, while Zone B might be desirable to minimize axial light reflectance, off axis light reflectance is better in Zone A. Above about 115 nm coating thickness in zone C, axial light reflections rise sharply. Accordingly, this zone is not as favorable as zones A or B with regard to axial light reflectance. Of the three zones, zone A appears to be the best region for minimizing off axis light reflections without significantly adversely affecting axial light reflectance or transmission. Accordingly, the present technology prefers zone A and coatings that have an overall thickness in the range from about 65 to about 85 nm.

Figure 5:
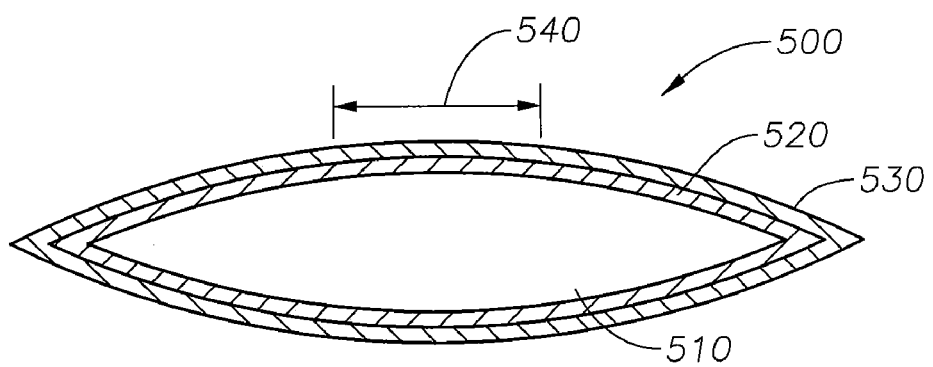
FIG. 5 is a cross section of an exemplary embodiment of an IOL lens body with a dual layered coating.

In other exemplary embodiments, the intraocular lenses have multiple layers, or at least dual layer, coatings that reduce off axis reflectance. FIG. 5 illustrates an IOL 500 with lens body 510 coated with a first coating layer 520. A second coating layer 530 is layered over the first coating layer 520. The first coating layer 520 is tightly adhered to the lens body 510. According to these embodiments, a first anti-reflective coating layer 510 has a refractive index $n_1$ that is less than the IOL lens body's refractive index $n_{IOL}$. The second anti-reflective coating layer 520, which is applied over the first anti-reflective coating layer 510, has a refractive index $n_2$ less than the refractive index $n_1$ of the first anti-reflective coating layer 520. In certain circumstances, dual-coated lenses may provide additional benefits. For example, the first coating layer may readily adhere strongly to the IOL lens body surfaces, and the second layer may adhere better to the first coating layer than to the IOL lens body material. Thus the use of two layers may enable a better coating from the standpoint of adherence to the lens body. In addition, multiple coatings provide a possibility of better performance in terms of reducing or eliminating reflections since each coating is optimal for a range of wavelengths, as is apparent from the above equations (A1) and (A2). The use of more than one coating provides greater flexibility or degrees of freedom in selection of each coating thickness and refractive index to achieve anti-reflectance.

Examples of embodiments of two-layer coated intraocular lenses present an advantage in being able to reduce reflections from off axis light by an order of magnitude (i.e., a factor of 10) or more. In exemplary embodiments with two coating layers applied, the first coating layer (i.e., the one in direct contact with the lens) may have a thickness in the range from about 65 to about 85 nm. The second coating layer may have a thickness in the range from about 45 to about 85 nm. Accordingly, overall coating thickness may range from about 110 to about 170 nm.

According to exemplary embodiments of the coated IOLs, the anti-reflective coating or dual coating may be applied to the entire IOL surface or only to peripheral areas and edges of the IOLs. Depending upon the process used to apply the coating or dual coating, the lenses may be masked to allow only the peripheral areas and edges to be coated. A variety of process may be used to apply the coating or dual coating. These include but are not limited to chemical vapor deposition, plasma assisted chemical vapor deposition, sputtering, spraying, dip-coating, or spin coating.

EXAMPLE

Example: Plasma coating of an IOL. The plasma chamber ring was coated with a single layer of allylamine (ALAM) plasma polymer. The allylamine monomer was added to a 50-ml round-bottom flask containing a magnetic stirrer. The round-bottom flask was connected to the plasma chamber with a vacuum take-off adapter attached to a stainless steel gas line. The flask and the adapter were tightly seated. A gas line was connected directly to the plasma chamber and gas flow rate was regulated through a metering valve. The flask was placed on a heating mantle, which was placed on a magnetic stirring plate. ALAM did not require heating to induce vaporization, but the mantle was gently heated to offset cooling of the flask due to expansion of the flask's contents under high vacuum. Temperature was maintained at 25° C. and was monitored by placing a thermocouple between the flask and the mantle.

The following stepwise procedure was used for the deposition of ALAM. The pressure in the vacuum chamber was reduced to less than 10 mTorr. The gas flow metering valve was opened and the chamber reached a pressure of 40 mTorr. Then the RF system was set to 200 Watts for 200 seconds. The process was then terminated and the chamber was allowed to return to atmospheric pressure.

The result was a lens with a 80 nm thick coating of allylamine polymer which was able to reduce off axis light reflectance by a factor of about 28 times compared to the uncoated lens.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

What is claimed is:

1. A coated intraocular lens, comprising:
a diffractive lens body having a first refractive index; and
an anti-reflective coating over at least a diffractive portion of the diffractive lens body, the anti-reflective coating comprising a first anti-reflective layer with a refractive index lower than a refractive index of the diffractive lens body and a second anti-reflective layer wherein the refractive index of the first anti-reflective layer is greater than a refractive index of the second anti-reflective layer and wherein the anti-reflective coating reduces an intensity of reflections produced from incident off axis light on the lens body by at least a factor of 2.5 times and wherein wherein the lens body is configured as a phakic IOL or as an IOL suitable for replacement of a natural crystalline lens.

2. The coated intraocular lens of claim 1, wherein the anti-reflective coating is about 65 to about 85 nm thick.

3. The coated intraocular lens of claim 1, wherein the first anti-reflective coating is tightly adhered to the lens body.

4. The coated intraocular lens of claim 1, wherein the first refractive index of the lens body is in the range from about 1.52 to about 1.60.

5. The coated intraocular lens of claim 1, wherein the anti-reflective coating reduces or eliminates an intensity of reflections produced from incident off axis light at least at edges of the lens body.

6. The coated intraocular lens of claim 1, wherein the anti-reflective coating reduces an intensity of reflections produced from incident off axis light on the lens body by at least a factor of about 28 times.

7. The coated intraocular lens of claim 1 wherein the anti-reflective coating is applied to only to peripheral areas and edges of the lens body.

8. A coated intraocular lens, comprising:
a lens body having a refractive index in the range from about 1.52 to about 1.60; and
an anti-reflective coating over at least a portion of the lens body, the anti-reflective coating comprising a first coating layer adhering to the lens body and a second coating layer adhering to the first coating layer, the first coating layer having a lower index of refraction than the lens body and the second coating layer having a lower refractive index than the first coating layer.

9. The coated intraocular lens of claim 8, wherein the anti-reflective coating reduces or eliminates an intensity of reflections produced from incident off axis light at least at edges of the lens body.

10. The coated intraocular lens of claim 8, wherein the anti-reflective coating reduces an intensity of reflections produced from incident off axis light on the lens body by at least a factor of about 28 times.

11. The coated intraocular lens of claim 8, wherein the anti-reflective coating is about 65 to about 85 nm thick.

12. The coated intraocular lens of claim 8, wherein the lens body comprises a diffractive lens body.

13. The coated intraocular lens of claim 12, wherein the anti-reflective coating reduces or eliminates an intensity of reflections produced from incident off axis light at least at edges of the lens body, the edges comprising sawtooth optical shapes.

14. The coated intraocular lens of claim 12 wherein the lens body is configured as a phakic IOL or as an IOL suitable for replacement of a natural crystalline lens.

15. The coated intraocular lens of claim 13 wherein the lens body is configured as a phakic IOL or as an IOL suitable for replacement of a natural crystalline lens.

16. The coated intraocular lens of claim 8, wherein the anti-reflective coating reduces an intensity of reflections produced from incident off axis light on the lens body by at least a factor of about 2.5 times.

* * * * *